United States Patent [19]

Hassan et al.

[11] Patent Number: 5,866,101
[45] Date of Patent: Feb. 2, 1999

[54] COLOR STABLE ANTICALCULUS COMPOSTION

[75] Inventors: Mahmoud Hassan, Piscataway; Kyle N. Brogden, Trenton; Gary Durga, Edison; Nagaraj S. Dixit, Plainsboro; Robert L. Mitchell, Somerset, all of N.J.

[73] Assignee: Colgate Palmolive Company, New York, N.Y.

[21] Appl. No.: 898,608

[22] Filed: Jul. 22, 1997

[51] Int. Cl.⁶ .................... A61K 7/16; A61K 7/18
[52] U.S. Cl. .................... 424/49; 424/52; 424/57
[58] Field of Search .......................... 424/49–58

[56] References Cited

U.S. PATENT DOCUMENTS

| | | | |
|---|---|---|---|
| 2,292,293 | 8/1942 | Rose | 260/635 |
| 3,927,202 | 12/1975 | Harvey et al. | 424/57 |
| 3,963,788 | 6/1976 | Kruse et al. | 260/635 C |
| 3,963,789 | 6/1976 | Kruse et al. | 260/635 C |
| 3,985,675 | 10/1976 | Kim | 252/317 |
| 4,357,314 | 11/1982 | Lynch . | |
| 4,381,318 | 4/1983 | Lynch | 426/658 |
| 4,435,380 | 3/1984 | Pader | 424/49 |
| 4,448,778 | 5/1984 | Lynch . | |
| 4,471,001 | 9/1984 | Lynch | 426/573 |
| 4,627,977 | 12/1986 | Gaffar et al. | 424/52 |
| 4,694,113 | 9/1987 | Gauthier et al. | 568/863 |
| 4,750,938 | 6/1988 | Cottrell | 106/35 |
| 4,923,684 | 5/1990 | Ibrahim et al. | 424/52 |
| 4,985,236 | 1/1991 | Ibrahim et al. | 424/52 |
| 5,145,667 | 9/1992 | Ibrahim et al. | 424/52 |
| 5,318,773 | 6/1994 | Winston et al. | 424/52 |
| 5,354,550 | 10/1994 | Collins et al. | 424/49 |
| 5,376,360 | 12/1994 | Domke et al. | 424/52 |
| 5,455,024 | 10/1995 | Winston et al. | 424/52 |
| 5,582,816 | 12/1996 | Mandanas et al. | 424/49 |
| 5,601,863 | 2/1997 | Borden et al. | 426/548 |

FOREIGN PATENT DOCUMENTS

| | | |
|---|---|---|
| 02212413 | 8/1990 | Japan . |
| 09037796 | 2/1997 | Japan . |

OTHER PUBLICATIONS

Kinoshita et al. J. Liq. Chromatgr. 14(10): 1929–1938 Ultra micro analysis of reducing and non–reducing sugars by liquid chromatergraphy, 1991.

*Primary Examiner*—Shep K. Rose
*Attorney, Agent, or Firm*—Paul Shapiro

[57] ABSTRACT

A storage stable oral composition having a pH of 8 or more which is effective against calculus, the composition containing an orally acceptable vehicle prepared using a sorbitol humectant containing less than about 0.10% by weight of a reducing sugar there being incorporated in the vehicle an effective anticalculus amount a water soluble alkali metal polyphosphate anticalculus salt.

7 Claims, No Drawings

COLOR STABLE ANTICALCULUS COMPOSTION

BACKGROUND OF THE INVENTION

1. Field of the Invention

The invention relates generally to an anticalculus dentifrice composition and more particularly to anticalculus dentifrice composition which is color stable on storage.

2. The Prior Art

Dental research has developed substantial evidence that beyond the age of 40 years loss of teeth is predominantly the result of periodontal involvement rather than dental caries. An important factor contributing to periodontal disease is the accumulation of dental calculus (e.g., salivary tartar) on the teeth. These deposits contribute to tissue inflammation of the surrounding gingiva, and, as the condition increases in severity, the supporting bone is also affected. These reactions lead to the destruction of the supporting structure and subsequent loss of teeth.

A wide variety of chemical and biological agents have been described in the art for retarding calculus formation or for removing calculus after it is formed. Included in the wide variety of chemical agents disclosed by the prior art as being effective as anticalculus agents are water soluble polyphosphate and pyrophosphate salts. For example, U.S. Pat. No. 4,627,977 discloses dentifrice composition containing one or a mixture of polyphosphate anticalculus salts such as water soluble alkali metal pyrophosphates, tripolyphosphates and hexametaphosphates, and a fluoride ion source, wherein salivary hydrolysis of P—O—P bonds in the polyphosphate salt is inhibited by the presence of 0.05 to 3 weight % of a polycarboxylate compound. When high concentrations of these polyphosphate salts are present in the dentifrice, e.g., 5–8% by weight, the pH of the dentifrice is in the alkaline range, i.e., in the range of about 8–10. U.S. Pat. No. 4,923,684 and U.S. Pat. No. 4,985,236 disclose the use of a water soluble alkali metal tripolyphosphate as an anticalculus agent contained in dentifrice compositions. The patent discloses that to be storage stable, the tripolyphosphate salt is incorporated in the dentifrice at a concentration of at least 4% by weight, the dentifrice having an alkaline pH, for example, a pH of 8–10.

In the preparation of the dentifrice compositions of containing high concentrations of polyphosphate anticalculus salts having an alkaline pH, it is desirable that sorbitol, in high concentrations, for example 30% by weight or more be used as a humectant as sorbitol is a relatively low cost material and imparts a desirable sweet flavor to the dentifrice. However, in dentifrice compositions in which the pH is above about 8, a browning discoloration of the dentifrice product is observed when commercially available sorbitol which normally contains 0.3% by weight reducing sugars such as mannitol is used in the dentifrice formulation. In addition to the undesirable discoloration of the product, an unpleasant flavor is imparted rendering the product undesirable for consumer use.

SUMMARY OF THE INVENTION

In accordance with the present invention, there is provided a storage stable oral composition having an alkaline pH which is effective against calculus which contains effective anticalculus amounts of a polyphosphate salt contained in an orally acceptable vehicle prepared using a high level of sorbitol humectant which is resistant to browning discoloration, the sorbitol having a reducing sugar content of 0.10% or less.

DESCRIPTION OF THE PREFERRED EMBODIMENTS

The vehicle used to prepare the dentifrice composition of the present invention is comprised of water and a humectants combination which sorbitol is a major constituent with other humectant such as glycerin, polyethylene glycol, or any suitable mixture thereof also being present in minor amounts.

Water is included in the vehicle of the dentifrice composition at a concentration of about 8% to about 25% by weight of the composition and preferably about 10 to about 25% by weight.

The proportion of vehicle used to prepare the dentifrice composition of the present invention is generally within the range of about 40 to about 70% by weight of the paste or gel dentifrice component of this invention and preferably about 50 to about 65% by weight of the dentifrice component. Sorbitol is present in the dentifrice vehicle of the present invention at a concentration of about 25 to about 60% by weight and preferably about 30 to about 40% by weight of the dentifrice composition. To avoid browning discoloration during storage, the sorbitols elected for use in the preparation of the vehicle of the present invention contains a reducing sugar content of about 0.10% by weight or less and preferably about 0.02 to about 0.07% by weight. The preparation of sorbitol containing a reducing sugar content of less than 0.1% by weight is known to the art and is disclosed for example in Gauthier et al, U.S. Pat. No. 4,694,113, the disclosure of which is herein incorporated by reference.

A surfactant is used in the preparation of dentifrice composition of the present invention to aid in prophylactic action and in the thorough dispersion of the dentifrice composition throughout the oral cavity when applied thereto as well as to improve the cosmetic acceptability and detersive and foaming properties of the dentifrice. Among the organic surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of olefin sulfonates, e.g. alkene sulfonates or hydroxalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine. The surfactant is included in the dentifrice composition of the present invention at a concentration of about 0.5 to about 3.0% by weight and preferably about 1.0 to about 2.0% by weight.

Polishing agents are incorporated in dentifrice composition of the present invention and include siliceous materials, such as precipitated amorphous hydrated silica, sodium bicarbonate, calcium carbonate, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, and calcined alumina. The polishing agent is present in the dentifrice composition of the present invention at a concentration of about 1.0 to about 30% by weight and preferably about 5 to about 25% by weight.

Inorganic thickeners may be included in the dentifrices of the present invention and include fumed silicas such as Cabosil available from Cabot Corporation, and thickening silicas including those available from J. M. Huber designated Zeodent 165. Organic thickeners such as natural and synthetic gums and colloids may also be incorporated in the dentifrice composition of the present invention examples of which include carrageenan (Irish moss), xanthan gum and sodium carboxymethyl cellulose (NaCMC), starch, polyvinylpyrrolidone, hydroxyethylpropylcellulose, hydroxybutyl methyl cellulose, hydroxypropyl methyl cellulose, and hydroxyethyl cellulose. The inorganic or organic thickener may be incorporated in the compositions of the present invention at a concentration of about 0.05 to about 3% by weight and preferably about 0.1 to about 2.5% by weight.

Fluoride-providing salts having anti-caries efficacy may also be incorporated in the dentifrice of the present invention and are characterized by their ability to release fluoride ions in water. It is preferable to employ a water-soluble salt fluoride providing about 10–2,000 ppm of fluoride ion, and preferably about 1000–1500 ppm of fluoride ion. Among these materials are water-soluble inorganic metal salts, for example, sodium fluoride, (NaF), potassium fluoride, sodium monofluorophosphate, (NaMFP) and sodium fluorosilicate. NaF and NaMFP are preferred fluorine-providing salts.

Pyrophosphate salts having anticalculus efficacy useful in the practice of the present invention include water soluble salts such as dialkali or tetra-alkali metal pyrophosphate salts such as $Na_4P_2O_7$ (TSPP), $K_4P_2O_7$, $Na_2K_2P_2O_7$, $Na_2H_2P_2O_7$ and $K_2H_2P_2O_7$. Polyphosphate salts include the water soluble alkali metal tripolyphosphates such as sodium tripolyphospahte (STPP) and potassium tripolyphosphate. The polyphosphate salts are incorporated in the dentifrice composition of the present invention at a concentration of about 4 to about 10% by weight and preferably about 5 to about 8% by weight.

There may also be included in the oral composition an anionic polymeric polycarboxylate compound having a molecular weight of about 1,000 to about 1,000,000, preferably about 30,000 to about 800,000 to promote the efficacy of polyphosphate salts as inhibitors of dental calculus. The polycarboxylate is generally employed in the form of its free acids or preferably as a partially or fully neutralized water soluble alkali metal salt, e.g., sodium, potassium or ammonium salts. Preferred are 1:4 to 4:1 copolymers of maleic anhydride or acid with another polymerizable ethylenically unsaturated monomer, preferably a methyl vinyl ether/ maleic anhydride copolymer having a molecular weight (M.W.) of about 30,000 to about 1,000,000, most preferably about 30,000 to about 500,000. These copolymers are available, for example, under the trademark Gantrez e.g., Gantrez AN 139 (M.W. 500,000), AN 119 (M.W. 250,000); and preferably Gantrez S-97 Pharmaceutical Grade (M.W. 700,000), of GAF Corporation. The polycarboxylate compound is incorporated in the compositions of the present invention in weight amounts of about 0.05 to about 3%, and preferably about 0.1 to about 2%.

Colorants such as pigments and dyes may be used in the practice of the present invention. Pigments include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)- Æ-3,5-cyclohexadienimine], FD&C Blue No. 1 (disodium salt of dibenzyldiethyl-diaminotriphenylcarbinol trisulfonic acid anhydrite), FD&C Blue No. 2(sodium salt of disulfonic acid of indigotin) and mixtures thereof in various proportions. The dyes are present in the dentifrice composition in an amount from about 0.05 percent to about 10 percent by weight with respect to the weight of the total dentifrice component and preferably present from about 0.0005 % to about 2 % by weight.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, orange and methyl salicylate. Suitable sweetening agents include sucrose, lactose, maltose, sorbitol, sodium cyclamate, perillartine, and sodium saccharin. Suitably, flavor and sweetening agents together comprise from 0.01% to 5% or more of the dentifrice composition.

Various other materials may be incorporated into the dentifrice composition of this invention. Non-limiting examples thereof include preservatives, silicones and chlorophyll compounds, antibacterial agents such as chlorohexidene, halogenated diphenyl ethers such as Triclosan, desensitizing agents such as potassium nitrate and potassium citrate and mixtures thereof. These adjuvants are incorporated in the dentifrice components in amounts which do not substantially adversely affect the properties and characteristics desired, and are selected and used in proper amounts, depending upon the particular type of dentifrice component involved.

To prepare the dentifrice composition of the present invention, the humectant, e.g., sorbitol, polycarboxylate compound and sweetener are dispersed in a conventional mixer until the mixture becomes a homogeneous gel phase. Into the gel phase are added, the anticalculus agents and a fluoride anticaries agent. These ingredients are mixed until a homogeneous phase is obtained. Thereafter the thickener, polishing agent, flavor and surfactant ingredients are added and the ingredients mixed at high speed under vacuum of about 20–100 mm Hg. The resultant product is a homogeneous, semi-solid, extrudable paste product.

The following examples illustrate this invention further. All proportions and amounts therein and elsewhere in this specification are by weight unless otherwise indicated.

EXAMPLE I

To assess the storage stability of the composition of the present invention, a series of dentifrice compositions designated "Compositions A–F" was prepared containing 1% TSPP and 7% STPP following the procedure previously described containing the ingredients listed in Table I below.

Each of Compositions A–F had a pH of about 9 when measured directly with a pH meter. Compositions A–C were prepared using a sorbitol humectant which had a reducing sugar concentration of 0.05% when assayed using a boiling mixture of cupric tartrate to form cupric oxide pursuant to the method disclosed at page 390 of Food Chemicals Codex, Fourth Edition, July 1996.

For purposes of contrast, Compositions D–F were prepared using a sorbitol humectant which had a reducing sugar content of 0.21%.

TABLE I

| Ingredients | Composition | | | | | |
|---|---|---|---|---|---|---|
| | A | B | C | D | E | F |
| Water | 11.00 | 11.00 | 14.00 | 11.00 | 11.00 | 14.00 |
| Glycerin | 10.00 | 10.00 | 12.00 | 10.00 | 10.00 | 112.00 |
| PEG 600 | 3.00 | 3.00 | — | 3.00 | 3.00 | — |
| Sorbitol (NB)* | 30.017 | 30.667 | 27.20 | — | — | — |
| Sorbitol (R)** | — | — | — | 30.217 | 30.667 | 27.20 |
| TSPP | 1.00 | 1.00 | 1.00 | 1.00 | 1.00 | 1.00 |
| STPP | 7.00 | 7.00 | 7.00 | 7.00 | 7.00 | 7.00 |
| Color | — | 0.40 | — | — | 0.40 | — |
| Gantrez S-97 (liq) | 7.69 | 7.69 | 7.69 | 7.69 | 7.69 | 7.69 |
| Saccharin | 0.40 | 0.45 | 0.40 | 0.40 | 0.45 | 0.40 |
| NaF | 0.243 | 0.243 | — | 0.243 | 0.243 | — |
| NaMFP | — | — | 0.76 | — | — | 0.76 |
| TiO$_2$ | 1.00 | — | 1.00 | 1.00 | — | 1.00 |
| Flavor | 0.95 | 0.85 | 1.00 | 0.95 | 0.85 | 1.00 |
| SLS | 1.20 | 1.20 | 1.20 | 1.20 | 1.20 | 1.20 |
| NaCMC | 1.10 | 1.10 | 1.10 | 1.10 | 1.10 | 1.10 |
| Iota Carrageenan | 0.40 | 0.40 | 0.40 | 0.40 | 0.40 | 0.40 |
| Sylodent-783 | 21.0 | 21.0 | 11.0 | 21.0 | 21.0 | 11.0 |
| Alumina | — | — | 10.0 | — | — | 10.0 |
| Zeodent-165 | 2.00 | 2.00 | 2.25 | 2.00 | 2.00 | 2.25 |

*Sorbitol (NB) = Sorbitol containing 0.05% reducing sugar.
**Sorbitol (R) = Sorbitol containing 0.21% reducing sugar.

The storage stabilities of compositions A–F were determined by loading the dentifrice compositions into plastic laminated tubes of the type used for commercial toothpastes, the tubes were then sealed and then aged at room temperature for varying time periods and temperatures. Thereafter, the tube contents were then examined visually and the degree of discoloration estimated by visual examination using a numerical discoloration rating scale in which 0=No discoloration noted
1=Trace discoloration
2=Slight discoloration
3=Moderate discoloration
4=Bad discoloration A numerical rating of 3 or more indicated that the discoloration evident in the sample examined was unacceptable for commercial acceptance. The numeral ratings are summarized in Table II below.

TABLE II

| | Composition | | | | | |
|---|---|---|---|---|---|---|
| | A | B | C | D | E | F |
| Temperature (Time) | Discoloration Numerical Rating | | | | | |
| 73° F. (6 months) | 1 | 1 | 1 | 3 | 3 | 3 |
| 105° F. (2 weeks) | 2 | 2 | 2 | 4 | 4 | 4 |
| 120° F. (8 weeks) | 2 | 2 | 2 | 4 | 4 | 4 |

The results recorded in Table II indicate that Compositions A–C which were formulated with sorbitol having a reducing sugar content of 0.05% in accordance with the practice of the present inventon experienced limited discoloration on aging at elevated temperatures whereas Compositions D–F sorbitol containing 0.21% reducing sugar experienced unacceptable discoloration when aged at elevated temperatures.

What is claimed is:

1. A dentifrice composition which is color stable during storage and is effective against calculus, the dentifrice having a pH of at least about comprising a vehicle prepared with about 25 to about 60% by weight of a sorbitol humectant having a reducing sugar content of less than about 0.10% by weight having incorporated in the vehicle about 5 to about 10% by weight of a water soluble alkali metal polyphosphate anticalculus salt.

2. The composition of claim 1 wherein the water soluble polyphosphate is sodium tripolyphosphate.

3. The composition of claim 1 wherein the alkali metal polyphosphate is sodium pyrophosphate.

4. The composition of claim 1 wherein a fluoride compound is incorporated in the vehicle.

5. The composition of claim 4 wherein the fluoride compound is sodium monofluorophosphate.

6. The composition of claim 1 wherein the pH is in the range between about 8 and 10.

7. The composition of claim 1 wherein the reducing sugar concentration is between about 0.02 to about 0.07% by weight.

* * * * *